United States Patent [19]

Tsukada

[11] Patent Number: 5,074,787
[45] Date of Patent: Dec. 24, 1991

[54] APPARATUS FOR PREVENTING INTERIOR CONTAMINATION OF HAND-PIECE

[76] Inventor: Yosiro Tsukada, 3-698, Hinatawada, Oome-shi, Tokyo, Japan

[21] Appl. No.: 284,123

[22] Filed: Dec. 14, 1988

[30] Foreign Application Priority Data

Oct. 25, 1988 [JP] Japan .................................. 63-268839

[51] Int. Cl.⁵ .............................................. A61C 1/02
[52] U.S. Cl. .................................................. 433/98
[58] Field of Search ...................... 433/28, 27, 80, 84, 433/85, 88, 89, 98, 99, 100; 415/503; 137/312

[56] References Cited

U.S. PATENT DOCUMENTS 3,511,264 5/1970 Krantz ................................ 433/100
3,903,916 9/1975 Waletzko ............................ 137/312

FOREIGN PATENT DOCUMENTS 1122310 11/1984 U.S.S.R. ................................ 433/28

Primary Examiner—Cary E. O'Connor
Attorney, Agent, or Firm—McGlew & Tuttle

[57] ABSTRACT

This apparatus is capable of preventing contamination in the interior of an airturbine hand-piece and its drive for use in dental treatment such as cutting a tooth. The apparatus comprises an airturbine drive air circuit, a discharge air circuit, and a chip air circuit for vaporizing cooled water, which serve as passageways for air at a relatively high pressure when the hand-piece is in operation and which are kept interiorly at a low air pressure when the hand-piece is out of operation. These passageways and change-over valves therefore are incorporated in a single body. When the hand-piece is inoperative upon completion of the treatment, it is possible to prevent various germs from penetrating from outside into the interior of the hand-piece. The apparatus can be reduced in a compact size and can be formed of plastics.

6 Claims, 4 Drawing Sheets

FIG. 3
FIG. 4a
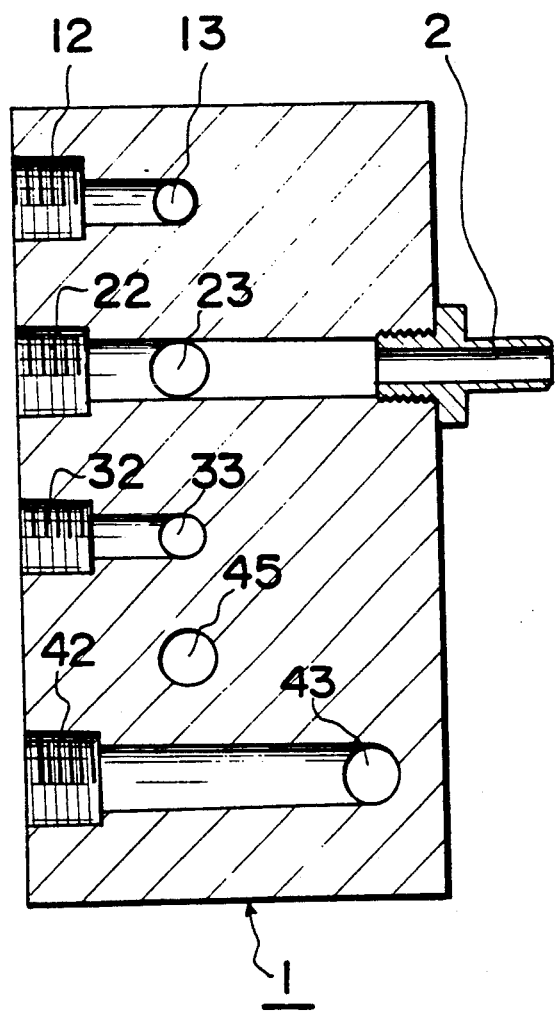
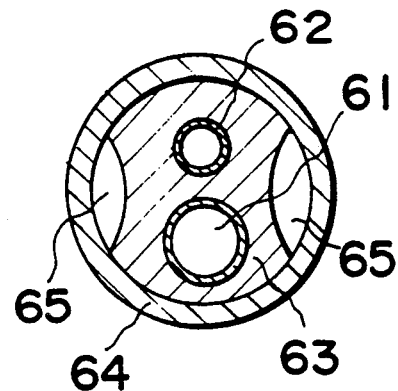
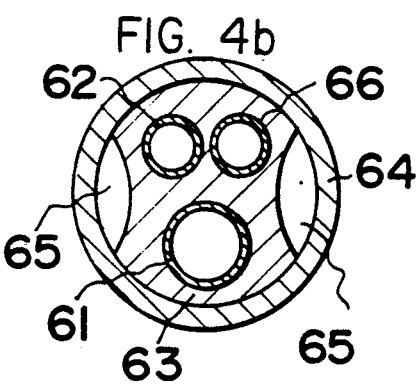
FIG. 4b
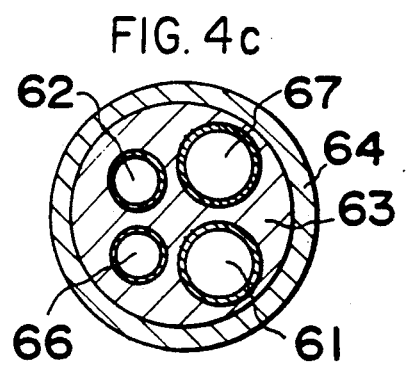
FIG. 4c

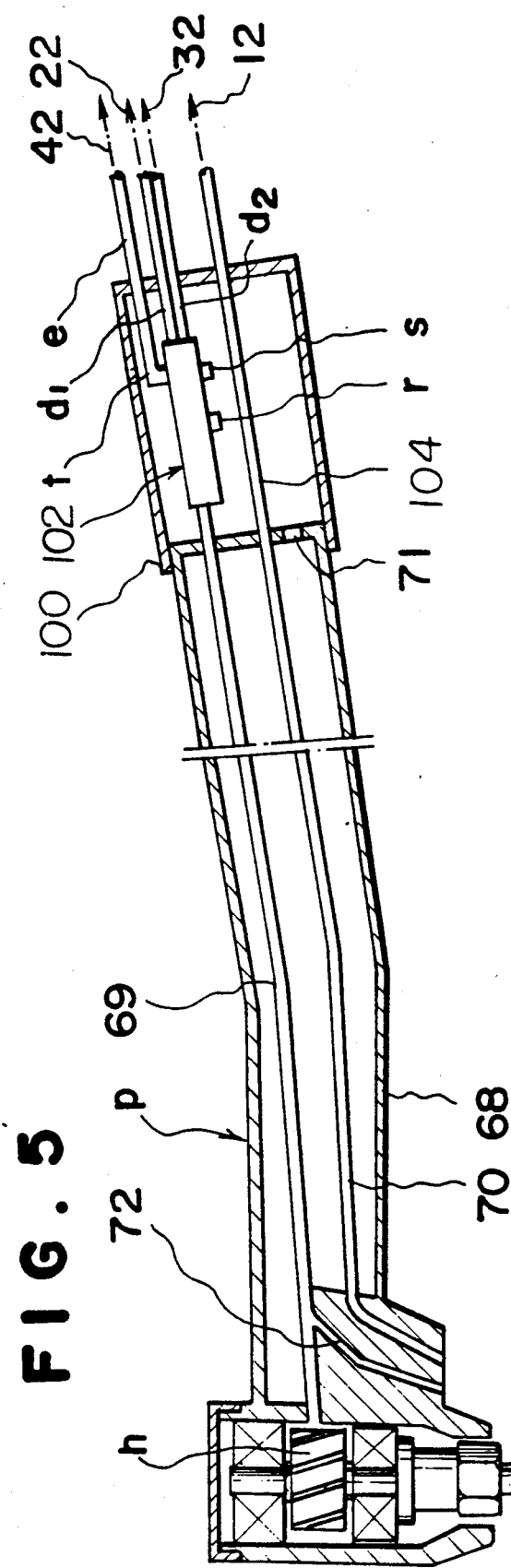
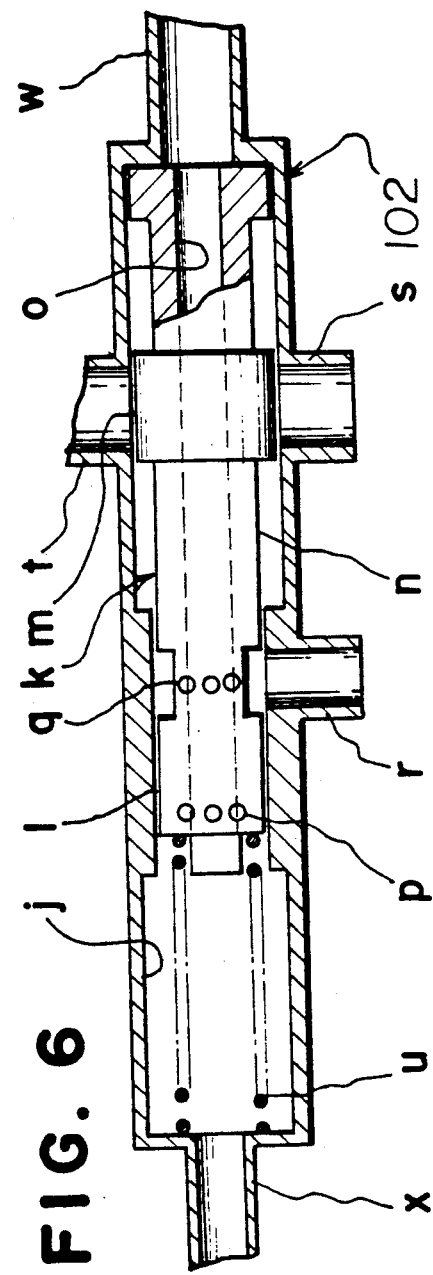
FIG. 5
FIG. 6

APPARATUS FOR PREVENTING INTERIOR CONTAMINATION OF HAND-PIECE

BACKGROUND OF THE INVENTION

The present invention relates to an apparatus for preventing any interior contamination of an air-turbine hand-piece and its drive mechanism for dental treatment such as cutting a tooth.

Conventionally, in practically available air-turbine hand-pieces for dental treatment, a high-pressure (2 to 4 kg/cm$^2$) air jet from an external pressurized air supply source is applied, via a supply pipe, on air-receiving blades of an air-turbine mounted on an end of the hand-piece, and is discharged from a discharge pipe; the air-turbine is thereby rotated at high speed (about 400,000 r.p.m.) to drive a cutting tool directly connected to the air-turbine.

Also, in order to prevent the cutting tool from developing heat and to wash away the chips of a tooth while the hand-piece is in use, cooled water jet is applied from an external water supply source to a blade tip of the cutting tool via a water pipe, and a tip air nozzle is juxtaposed to the discharge end of the water pipe for jetting an air stream to vaporize the cooled water.

In the hand-piece in which the cutting tool is rotating at high speed, in order to avoid the risk of contacting the inside skin of a mouth when the cutting tool is removed out of the mouth upon termination of the treatment of the interior of the mouth, it has been a common practice to discontinue supplying air to the airturbine to thereby stop rotation of the cutting tool at a working position.

However, after the supply of air to the airturbine rotating at high speed is stopped, the air-receiving blades continues rotating by inertia for a while, and therefore, a phenomenon causing a negative pressure occurs in the interior of the hand-piece.

As a result, at the tip of hand-piece assuming the working position, the cooled water attached to a chuck portion of the cutting tool and other parts is sucked into the structure of the hand-piece as dirty water containing the chips of a tooth, saliva, blood, various germs, etc, thus causing a contamination of the interior of the hand-piece.

This interior contamination due to the negative pressure phenomenon extends to a supply pipe connected to the hand-piece, to a discharge pipe, to a chip air pipe, and to a water pouring pipe. Further, the contamination occasionally extends to the mechanism for controlling the supply and discharge of air or water through these pipes.

Consequently, though only the airturbine at the tip of the hand-piece is removed from the mechanism after completion of the treatment and is then disinfected, the interior of the airturbine can be contaminated again from the air and water supply side as air and water are supplied to the hand-piece via the individual pipes for the next treatment, thus making the previous disinfection of the turbine wasteful.

Under these circumstances, only the effective disinfection of this kind of hand-piece is to prevent the interior of the hand-piece from being contaminated.

To this end, the most suitable measure for preventing this contamination of the interior of the hand-piece is to maintain the interior of the hand-piece at positive pressure so as to keep various germs from entering into the interior of the hand-piece from outside.

Most of existing modern dental treatment chairs are furnished with various tools as well as the drive mechanism for the airturbine hand-piece. Since these furnished tools are arranged in order and united in a compact form so as to facilitate the treatment, it is very difficult to additionally furnish on the chair a control mechanism composed of several air and electromagnetic valves which keeps the interior of the hand-piece a positive pressure after completion of the treatment.

Therefore, this kind of mechanism must be minimized both in size and in weight, or it cannot be practically useful.

With the foregoing problems in view, the present inventor developed a practically useful apparatus (Japanese Utility Model Application No. 146230/1987) which prevents the interior of airturbine hand-piece from being contaminated and with which various functions required to this kind of apparatus can be accomplished.

An air change-over circuit unit for supplying the pressurized air (0.1 to 0.3 kg/cm$^2$) required to keep the interior of the hand-piece at positive pressure, when the supply of the pressurized air of 2 to 4 kg/cm$^2$ pressure required to operate the hand-piece is stopped, must be operable to shift individually at least three system circuits, namely, an air supply circuit, an air discharge circuit and a chip air circuit. As a consequence, if this change-over circuit unit was composed of conventional ordinary air valves or three-direction valves, it would have been a complex passageway assembly.

Therefore, in the above-mentioned apparatus developed by the present invention, since conventional ordinary valves are used, the passageways are complicated so that the block body is required to be provided with many longitudinal and transverse passageways. Further, the passageways must be arranged in high density in the block body as it is desired to make the entire size of the apparatus compact, and for this reason, such complex passageways assembly must be manufactured carefully with high-degree perforation technology. Furthermore, the assembly must be manufactured by using as material a metal that is easy to process.

However, metal materials can be easily oxidated. Assuming that the hand-piece is dipped in a sterilization liquid for a long period of time due to the failure of switching on a low-pressure air to keep the interior of the hand-piece at a constant pressure, the sterilization liquid fills in the interior of the hand-piece and occasionally flows reversely through the air pipe to reach the block body.

In the sterilization liquid in this case, sodium hypozinc acid which is strong in oxidation to metal, is occasionally used so that rust develops in the passageways in the block body as well as in the air valve. This rust would impede the operation of the tools.

SUMMARY OF THE INVENTION

It is therefore an object of the present invention to provide an apparatus for preventing the interior of a hand-piece from being contaminated, which apparatus enables a simple construction of circuits and which apparatus is compact in size.

Another object of the invention is to provide an apparatus for preventing the interior of a hand-piece from being contaminated, in which apparatus the change-over operation of circuits can be made instantanously.

According to the present invention, an apparatus, for preventing the interior of an airturbine hand-piece from being contaminated, comprising an airturbine drive air circuit, a discharge air circuit, and a chip air circuit for vaporizing cooled water, the drive air circuit, the discharge circuit and the chip air circuit serving as passageways for air at a relatively high pressure when the hand-piece is in operation and being kept interiorly at a low pressure of air when out of operation, wherein each of the drive air circuit, the discharge circuit, the chip air circuit, and a low pressure circuit for passage of air at a low pressure is connected exteriorly to a pair of piston valves mounted on opposite ends of a cylinder having a midportion to which a common passageway extending toward the hand-piece is opening, each of the drive air circuit, the discharge circuit, the chip air circuit and the low pressure circuit thereby constituting a change-over circuit, and wherein the pair of piston valves in the drive air circuit and the chip air circuit is disposed s as to open toward one another, and wherein the pair of piston valves in the discharge circuit is disposed so as to open in a common direction.

With this arrangement, the individual change-over circuit composed of the pair of piston valves is operable in such a manner that one of the piston valves to which high pressure air is given is opened, while the other piston valve is closed.

Accordingly, in each change-over circuit, the air supply circuit and the chip air circuit send high-pressure drive air and high-pressure chip air to each of the air supply pipes of the hand-piece during the treatment by the hand-piece, and the discharge circuit is still high in opened, and at high residual pressure, in which condition return air from of the hand-piece id discharged to the atmosphere.

When the supply of drive air and chip air is stopped upon termination of the treatment, the direction in which pressure is applied to the pair of piston valves in each of the above-mentioned circuits is reversed so that these circuits are changed over instantanously to supply low pressure air. That is, a pair of cylinder valves has a midportion at which a common passageway extending toward the hand-piece opens to the cylinder, and serves as a shuttle valve and a check valve with resepct to the pressurized air.

Many other advantages, features and additional objects of the present invention will become manifest to those versed in the art upon making reference to the detailed description and the accompanying drawings in which a preferred structural embodiment incorporating the principles of the present invention is shown by way of illustrative example.

BRIEF DESCRIPTION OF THE DRAWINGS

FIG. 3 is an enlarged horizontal cross-sectional view taken along line B—B in FIG. 1;

FIGS. 4(A), 4(B) and 4(C) are enlarged cross-sectional views of various kinds of hand-pieces;

FIG. 5 is an enlarged longitudinal cross-sectional view of an adaptor connected to a two-hole-type hand-piece; and FIG. 6 is enlarged longitudinal cross-sectional view of relay tube incorporated in the adaptor of FIG. 5.

DETAILED DESCRIPTION OF THE PREFERRED EMBODIMENT

The principles of the present invention will be particularly useful when embodied in an apparatus for preventing the interior of an airturbine hand-piece from being contaminated (hereinafter called "apparatus"), the apparatus being entirely shown in FIG. 1.

Figure 1:
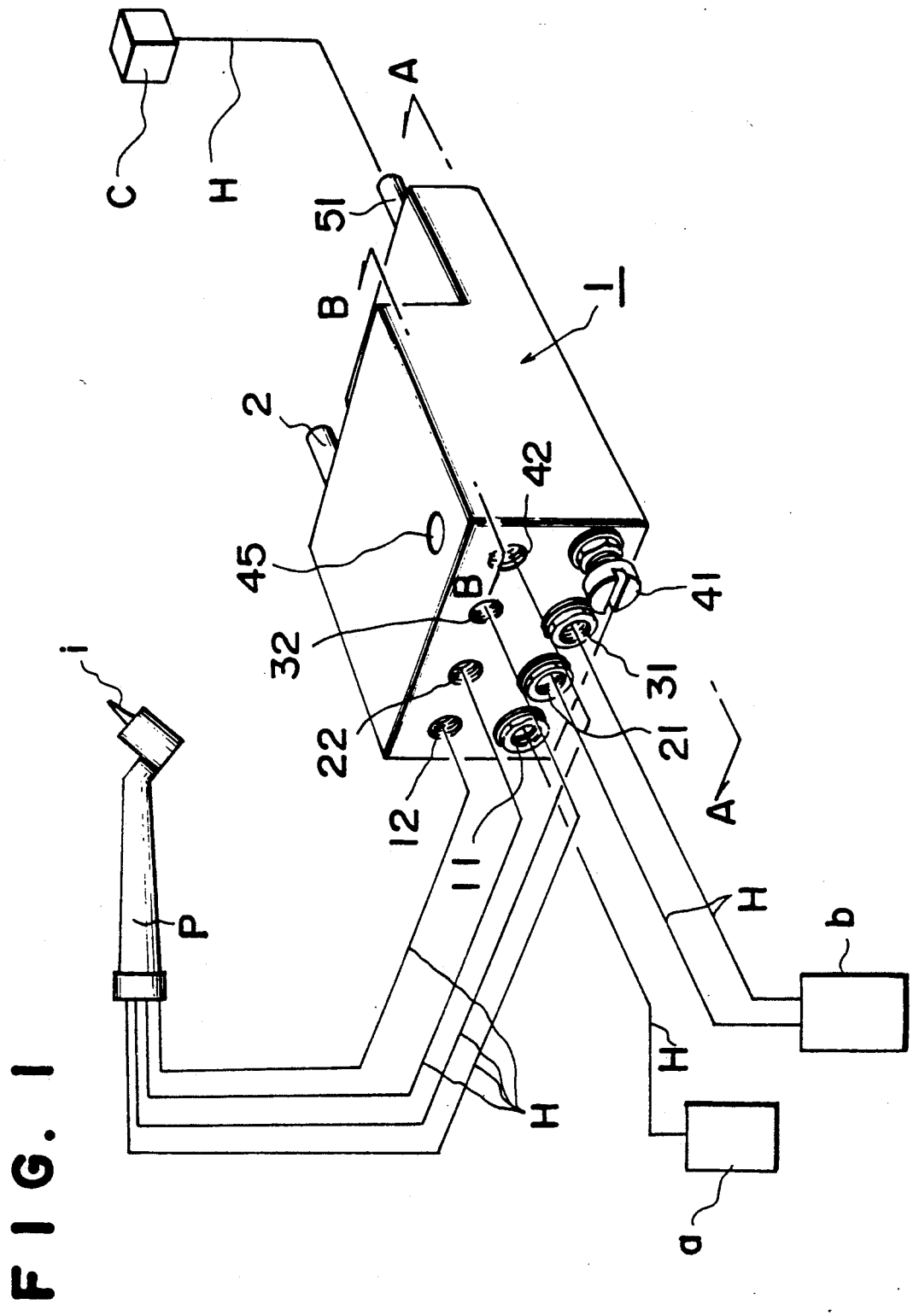
FIG. 1 is a perspective view of a handpiece-contamination preventing apparatus according to an embodiment of the present invention.

As shown in FIG. 1, the apparatus comprises a body 1 made of Derlin (tradename) or other chemical resistant plastic material. The body 1 is in the form of a block having at one end a cut-away stepped portion. A pressure gauge mounting port 2 projects from an upper step end surface of the stepped portion of the block body 1, and a low-pressure supply inlet port 51 projects from a lower step end surface of the stepped portion of the block body 1. At a lower portion of the other end surface of the block body 1, a water supply port 11, a drive air inlet port 21, a chip air inlet port 31 and an air discharge adjusting cock 41 are arranged in row in this order. Likewise, at an upper portion of the other end surface of the block body 1, a water supply outlet port 12, a drive air outlet port 22, a chip air outlet port 32 and a discharge air introduction port 42 are arranged in row in this order, one for each relay hose H adapted to be connected to a hand-piece P.

Figure 2:
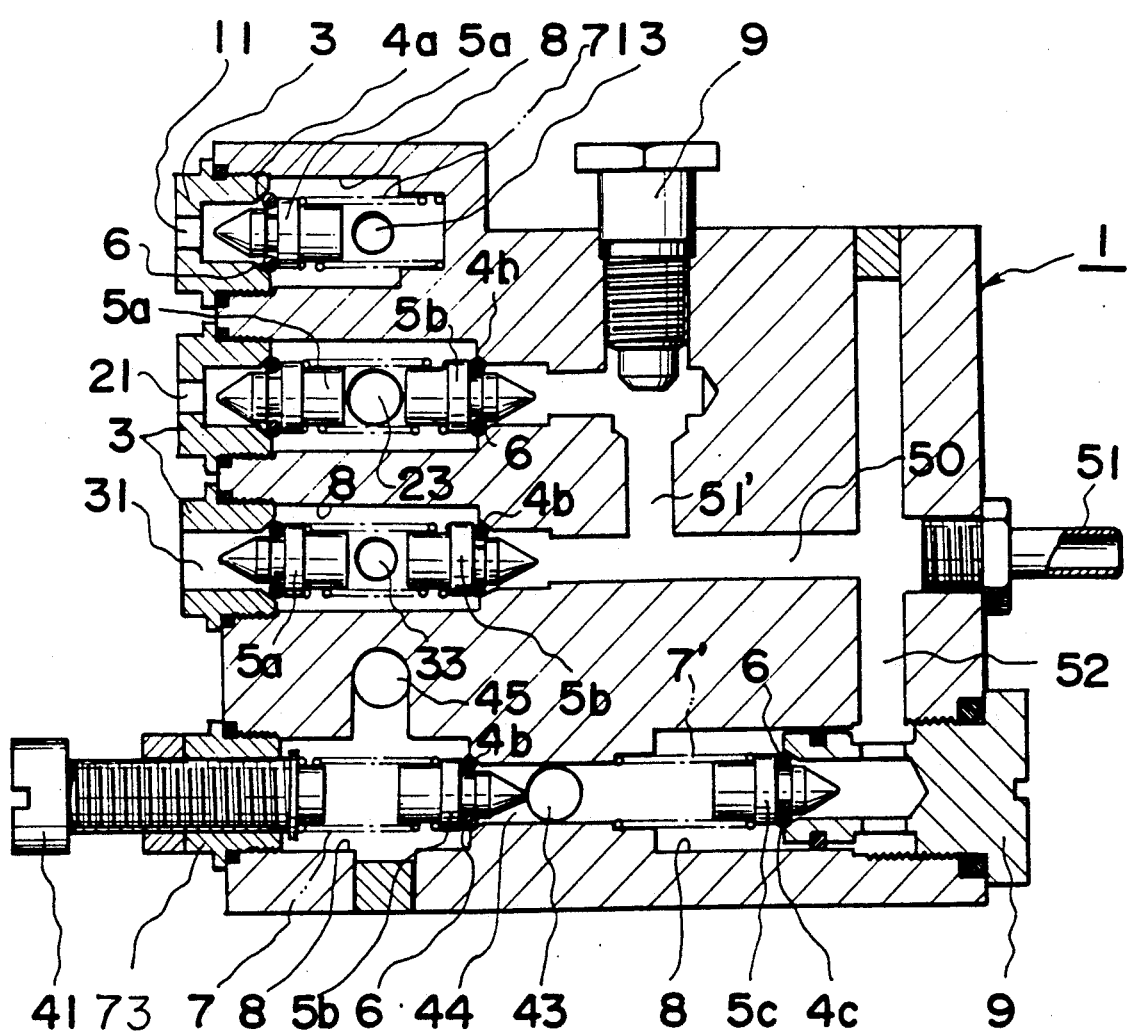
FIG. 2 is an enlarged horizontal cross-sectional view taken along line A—A in FIG. 1.

As shown in FIG. 2, each of the water supply port 11, the drive air inlet port 21 and the chip air inlet port 31 includes a pipe sleeve 3 threadedly fitted in a peripheral edge of a valve socket formed in the block body 1. The inner end of each pipe sleeve 3 is tapered to provide a valve seat 4a, against which a tip of poppet piston 5a in the form of a cone-shaped piston valve is disposed for closing and opening the valve. An O-ring is mounted on the forward end of the piston 5a and is normally urged against the valve seat 4a by a weak biasing force of a spring 7, thus providing a valve mechanism in each of the water supply circuit, the drive air circuit and the chip air circuit.

Further, in the valve socket of each of the drive air circuit and the chip air circuit, an inner end of each cylinder 8 is provided with a similar valve seat 4b, and another similar piston 5b is disposed in confronting relation to the piston 5a in such a direction that a tip of the piston 5b is normally urged against the valve seat 4b. Designated by 9 is a low-pressure air adjusting cock.

At its midportion, the cylinder 8 of each of the water supply circuit, the drive air circuit and the chip air circuit communicates with a passageway 13, 23, 33 communicating with the respective outlet port 12, 22, 32 adapted to be connected to the hand-piece P.

In a discharge air circuit having the air discharge adjusting cock 41, the discharge adjusting cock 41 is threadedly fitted in the pipe sleeve 31 and extends into the cylinder 8 to throttle the discharge air passageway 45 opening to the side passageway of the cylinder 8. The inner end of the cylinder 8 is provided with a similar valve seat 4b, and another piston 5b is disposed in confronting relation to the discharge adjusting cock 41 in such a direction that a tip end of the piston 5b is normally urged against the valve seat 4b, thus providing a valve mechanism. Additionally, a valve seat member 4c is mounted in an extension passageway 44 of the cylinder 8, and a further piston 5c is disposed in the extension passageway 44 and is normally urged at its tip against the valve seat member 4c under the biasing force of a spring 7'. A passageway 43 communicating with the discharge air introduction port 42 adapted to be connected to the air discharge hose H extending from the hand-piece P is opening to a midportion of the extendion passageway 44 of the cylinder 8 between these two pistons 5b, 5c.

Further, a low-pressure air supply circuit communicating with the low-pressure air supply inlet port 51 is connected to the outside of the piston 5b, 5c of each circuit via passageways 50, 51', 52.

FIG. 3 illustrates the manner in which each of the water supply outlet port 12, the drive air outlet port 22, the chip air outlet port 32 and the discharge air introduction port 42 is connected to the respective passageways 13, 23, 33, 43, and also the manner in which the pressure gauge mounting port 2 is communicating with the drive air outlet port 22.

In operation, before starting the apparatus, the hose H extending from each of the water supply source a, the high-pressure air supply source b and the low-pressure air supply source c is connected to the respective inlet port 11, 21, 31, and the respective hose H extending from the hand-piece P is connected to each of the outlet and introduction ports 12, 22, 32, 42. As the apparatus is started, pressurized water from the water supply source a reaches the water supply inlet port 11 to push each piston 5a rightwardly in FIG. 2 against the biasing force of the respective spring 7 to open the respective valve so that the pressurized water flows from the water supply outlet port 12 toward the pouring pipe of the hand-piece P via the gap in the cylinder 8.

Concurrently, pressurized air from the high-pressure air supply source a reaches the drive air inlet port 21 and the chip air inlet port 31 to push each piston 5a of these two systems against the biasing force of the respective spring 7 to open the respective valve so that the pressurized air or drive air from the drive air outlet port 22 toward the airturbine of the hand-piece P via the passageway 23 and the hose H, while the chip air flows from the chip air outlet port 32 toward the chip air pipe of the hand-piece P via the passageway 33 and the hose H.

At that time, the other piston 5b in each system is urged rightwardly in FIG. 2 by the biasing force of the spring 7 and the interior pressure of the cylinder 8 due to the highly pressurized air, thus urging the O-ring 6 against the valve seat 4b to close the valve. Therefore, although the low-pressure air normally imparted to the low-pressure air supply port 51 acts on the piston 5b in such a direction (leftwardly in FIG. 2) as to open the valve, the pistons 5b are kept in closed position.

Consequently, a large amount of relatively highly pressurized air reaches the airturbine of the hand-piece P from the drive air outlet port 22 via the drive air inlet port 21 of the body 1 and the piston 5a. After striking the turbine and the cutting tool i to drive them, the pressurized air is returned to the discharge air introduction port 42 of the body 1 from the discharge air hose H and is thence blown into the longitudinal hole 44 via the passageway 43 to act on the piston 5c, together with the biasing force of the spring 7', in such a direction as to close the valve. The pressurized air also acts on the other piston 5b to push the same leftwardly in FIG. 2 against the biasing force of the spring 7 to open the valve, and then the pressurized air is discharged from the discharge air port 45 to the atmosphere.

By the foregoing operation, at the tip of the hand-piece P, the cutting tool i driven by the airturbine is rotated at high speed and, at the same time, cooled water is discharged toward the cutting tool i. The cooled water is vaporized by the chip air to wash away tooth chips, with cooling the cutted surface of the tooth.

As the supply of the cooled water, the high-pressure drive air and the chip air is stopped concurrently with the completion of the treatment, the supply pressure to the cooled water inlet port 11 is lowered. As a result, the piston 5a in the cooled water circuit is moved by the biasing force of the spring 7 so as to close the valve, and likewise, the piston 5a in each of the drive air circuit and the chip air circuit is moved so as to close the valve.

In each air circuit, the internal pressure of the cylinder 8 is lowered due to the termination of the pressure supply, and the other piston 5b is moved, due to the relatively low air pressure imparted to the low-pressure air circuit 50 and passageway 51, to close the valve. Therefore, the supply of low-pressure air is instantaneously substituted for the previous supply of high-pressure air.

Meanwhile, also in the discharge air circuit, when the return of the high-pressure discharge air flow is stopped, the piston 5b is moved to close the valve and, at the same time, the piston 5c is pushed by the low-pressure air supply of the previous low-pressure air supply circuit and passageway 52 to open the valve so that the low-pressure air flows also to the discharge air circuit. At that time, since the pressure air flows, contrary to the ordinary case, from the introduction port 43 reversely to the tip of the hand-piece, the pressure air strikes the low-pressure air reached the airturbine via the drive air circuit, thus controlling the airturbine.

Moreover, since the change-over of each air circuit to the low-pressure air supply is made while the air pressure of the circuit is being lowered due to the disconnection of the high-pressure air supply during the treatment, namely, under the positive pressure before the atmosphere, these air circuits will never be placed under the negative pressure so that various germs outside the hand-piece P can be prevented from being sucked into the hand-piece P.

The existing hand-pieces can be classified into the following types: a two-hole type (FIG. 4(A)) composed of an outer casing 64, and a core member 63 received in the outer casing 64 and having an air supply pipe 61 and a water pouring pipe 62, there being defined between the outer casing 64 and the core member 63 a pair of air discharge grooves 65; a three-hole type (FIG. 4(8)) in which the core member 63 has, in addition to the air supply pipe 61 and the water pouring pipe 62, an independent chip air pipe 66; and a four-hole type (FIG. 4(C)) in which the core member 63 has also an air discharge pipe 67 in place of the air discharge grooves 65.

In the apparatus of FIG. 1, since the four ports, i.e., the water supply port 12, the drive air outlet port 22, the chip air outlet port 32 and the discharge air introduction port 42 are connected to the respective hand-piece P via the respective hoses H, the four hoses H of the four-hole-type hand-piece of FIG. 4(C) can be connected to the respective four ports. However, this apparatus cannot be adapted to the two-hole-type or three-hole-type hand-piece because of the difference in the number of holes and the number of circuits.

According to the present invention, as shown in FIGS. 5 to 8, an adaptor, or together with a connector, is mounted on the end of the hand-piece P so that the four circuits of the apparatus of the present invention can be connected to either the two-hole-type or three-hole-type hand-piece.

FIG. 5 shows an example in which the apparatus of the present invention is connected to the two-hole-type hand-piece P via an adaptor 100. The adaptor a is detachably connected to the hand-piece P, and in the adaptor a, a relay tube 102 and a water pouring tube 104 are mounted. The relay tube b is connected to the drive air outlet port 22 and the chip air outlet port 32 via a pair of air supply pipes $d_1$, $d_2$, respectively, and is also connected to the discharge air introduction port 42 via an air discharge pipe e. The water pouring tube 104 is connected to the water supply port 12.

In a grip body 68 of the hand-piece P, an air supply pipe 69 and a water pouring pipe 70 are mounted. A chip air pipe 72 is branched from the air supply pipe 69.

As high-pressure air is supplied to the air supply pipe 69, this air drives the blades h to rotate the cutting tool i. At that time, a portion of the high-pressure air is discharged from the outer periphery of the cutting tool i, while the remaining portion of the high-pressure air is discharged into an air discharge groove 71 via a hollow portion of the grip body 68.

The cooled water supplied to the water pouring pipe 70 is jetted toward the cutting tool i and is vaporized by the air jetted from the chip air pipe 72.

The relay tube 102 is fixed mounted in the adaptor 100 such as by means of a bracket. As shown in FIG. 6, the relay tube 102 has a hollow portion j in which a piston k is movably inserted and is normally urged rightwardly under the biasing force of a spring u.

The piston k has a central air passageway o, a pair of ports p, q opening to the air passageway o, and three lands l, m, n.

Five pipes r, s, t, w, x opens to the hollow portion j of the relay tube 102. The pipes r, s open to the interior of the adaptor 100 and comminicate with the discharge air groove 71, and the pipe t is connected to the discharge air pipe e. The pipe w is connected to the air supply pipes $d_1$, $d_2$, and the pipe x is connected to the air supply pipe 69.

During the reciprocating movement, lands l, n close and open the ports p, q, and the land m closes and opens the pipes s, t. As the piston k is moved leftwardly against the biasing force of the spring u, port p opens to the pipe x via the hollow portion J of the relay tube b, and the port q is closed with respect to the pipes r; at that time, the pipes s, t communicate with one another.

On the other hand, as the piston k is moved rightwardly as shown in FIG. 6, port p is closed, and the other port q opens to the pipe r, shutting off the pipes s, t.

The pipes s, t communicate with one another via the hollow portion j of the relay tube 102 when the land m is moved leftwardly. Alternatively, the pipes s, t may communicate directly with one another.

In operation, as drive air and chip air are supplied, the air is introduced to the relay tube b from the air supply pipes $d_1$, $d_2$ via the pipe w to the piston k leftwardly against the biasinf force of the spring u. This air is further introduced to the pipes x via the passageway o and the port p in the piston k. The air is blown to the blades h via the air supply pipe 69 to drive the blades h. The return discharge air having driven the blades h is discharged to the atmosphere from the discharge air introduction port 42 via the hollow portion of the grip body 68, the air discharge groove 71, the interior of the adapter 100, the pipe s, the hollow portion j of the relay tube 102, the pipe t and the air discharge pipe e.

Upon termination of the treatment, the supply of the drive air and the chip air is stopped. Instead of the drive air and the chip air, as low-pressure air of 0.2 kg/cm$^2$, for example, is supplied to the air discharge pipes $d_1$, $d_2$, the piston k is moved rightwardly by the biasing force of the spring u against the air pressure to cause the port q to open to the pipe r. The low-pressure air is thereby blown to the blades h via the passageway o, the port q, the interior of the adaptor 100 and the air discharge groove 71 to brake the blades h and also to keep the interior of the grip body 68 and the interior of the adaptor 100 at positive pressure, thus preventing any dirty water from penetrating the grip body 68 and the adaptor a.

The construction of the adaptor is not limited to the illustrated embodiment. For using the three-hole-type hand-piece, a connector, in addition to the adaptor, may be connected to the apparatus.

According to the apparatus of the present invention, the valve mechanism, in each of the drive air circuit communicating the tip of the hand-piece, the chip air circuit and the discharge air circuit, for making a change-over between the high-pressure condition during the treatment and the low-pressure condition upon completion of the treatment, includes a pair of piston valves at the opposite ends of the cylinder, and a common passageway disposed between the pair of piston valves. With this arrangement, since the piston valve on which the high-pressure air is applied is moved to open the valve and, to the contrary, the other piston valve is moved to close the valve, so that each of the drive air circuit, the chip air circuit and the discharge air circuit can be communicated with the hand-piece via the common passageway.

In shifting from the high-pressure condition to the low-pressure condition in the apparatus of the present invention, as the internal pressure of the cylinder between the pair of piston valves starts lowering to a value slightly below the low air pressure, the high-pressure piston valve is pushed to open so that the supply of the low-pressure air is automatically initiated. At that time, since the piston valve is movable so as to open to a minimum extent, each air pipe of the tip of the hand-piece is shifted to the low-pressure air supply condition under the positive pressure condition before lowering to the atmosphere, thus not only controlling the airturbine, but also keeping the turbine and the associated pipes at the positive pressure to prevent the same parts from being contaminated.

Another advantage of the apparatus of the present invention is that because the circuits in the valve mechanism are simple in construction, the passageways in the body can be bored or otherwise formed relatively easily, and synthetic resin can be used as material for the body. Using synthetic resin for the body, it is possible to obtain a valve mechanism which is resistant to corrosion by oxidation.

What is claimed is:

1. An apparatus for preventing the interior of an airturbine hand-piece from being contaminated, comprising an airturbine drive air circuit, a discharge air circuit, and a chip air circuit for vaporizing cooled water, the drive air circuit, the discharge air circuit and chip air circuit serving as passageways for air at a relatively high pressure when in operation and being kept interiorly at a low pressure air when out of operation, wherein each of the drive air circuit, the discharge air circuit, the chip air circuit, and a low pressure circuit for air at a low pressure is connected exteriorly to a pair of piston valves mounted on opposite ends of a cylinder having a midportion to which a common passageway extending toward the hand-piece opens, each of the drive air circuit, the discharge air circuit, the chip air circuit and the low pressure circuit thereby constituting a change-over circuit, and wherein the pair of piston valves in the drive air circuit and the chip air circuit is disposed so as to open toward one another, and wherein the pair of piston valves in the discharge air circuit is disposed so as to open in a common direction.

2. An apparatus according to claim 1, wherein the apparatus includes a body made of Derlin (tradename) or other chemical resistant plastic material.

3. An apparatus according to claim 1, wherein each of the pair of piston valves disposed at opposite ends of a cylinder is a poppet piston, and wherein a high pressure acts outwardly on one of such two pistons, and a low pressure acts outwardly on the other piston.

4. An apparatus according to claim 1, wherein the apparatus includes a single body in which the passageways constituting the drive air circuit, the discharge air circuit, the chip air circuit and the low-pressure air supply circuit are incorporated.

5. An apparatus according to claim 1, wherein the drive air circuit, the discharge air circuit and the chip air circuit are connected to the hand-piece directly.

6. An apparatus according to claim 1, wherein the drive air circuit, the discharge air circuit and the chip air circuit are connected to the hand piece by a corresponding adaptor.

* * * * *